(12) United States Patent
Weisburg et al.

(10) Patent No.: US 6,482,589 B1
(45) Date of Patent: Nov. 19, 2002

(54) NUCLEIC ACID PROBES FOR THE DETECTION OF GENITAL MYCOPLASMAS

(75) Inventors: William G. Weisburg, Milford, MA (US); Dale A. Pelletier, Brighton, MA (US)

(73) Assignee: Vysis, Inc., Downers Grove, IL (US)

( * ) Notice: Subject to any disclaimer, the term of this patent is extended or adjusted under 35 U.S.C. 154(b) by 0 days.

(21) Appl. No.: 08/452,129

(22) Filed: May 26, 1995

Related U.S. Application Data (62) Division of application No. 07/673,661, filed on Mar. 22, 1991.

(51) Int. Cl.[7] ............................ C12Q 1/68; C12P 19/34; C07H 21/02
(52) U.S. Cl. .............................. 435/6; 435/6; 435/91.2; 536/22.1; 536/23.1; 536/24.3; 536/24.31; 536/24.32
(58) Field of Search ................... 435/6, 91.2; 536/22.1, 536/23.1, 24.3, 24.31, 24.32

(56) References Cited

U.S. PATENT DOCUMENTS

| | | | | |
|---|---|---|---|---|
| 5,288,611 A | * | 2/1994 | Kohne et al. ................... | 435/6 |
| 5,401,631 A | * | 3/1995 | Lane et al. ..................... | 435/6 |
| 5,843,667 A | * | 12/1998 | Weisburg et al. ............... | 435/6 |

FOREIGN PATENT DOCUMENTS

| | | | |
|---|---|---|---|
| WO | WO 88/03957 | * | 6/1988 |

OTHER PUBLICATIONS

Gobel et al, "Oligonucleotide probes complementary to variable regions of ribosomal RNA discriminate between Mycoplasma species", J. Gen. Microbiol. 133: 1969–1974, 1987.*
Weisburg et al, "A phylogenetic analysis of the mycoplasmas: Basis for their classification", J. Bacteriol. 171 (12):6455–6467, Dec. 1989.*
Hata et al, "Evaluation of DNA probe test for rapid diagnosis of Mycoplasma pneumoniae infections", J. Pediatrics 116(2):273–276, Feb. 1990.*
Fraser et al, "The minimal gene complement of Mycoplasma genitalium", Science 270:397–403, Oct. 1995.*
Joklik et al, Zinsser Microbiology, Appleton Century Crofts, Norwalk, Connecticut, p. 794, 1984.*

* cited by examiner

Primary Examiner—Jeffrey Fredman
(74) Attorney, Agent, or Firm—Norval B. Galloway (57) ABSTRACT

Nucleic acids having approximately 10 to 250 nucleotides which are capable of hybridizing to rRNA and RDNA of mycoplasma etiological agents of nongonococcal urethritis, pelvic inflammatory disease, salpingiuis, and other infections due to mycoplasmas from the genital areas, *Mycoplasma hominis, Mycoplasma genitalium*, and *Ureaplasma urealyticum*.

11 Claims, 1 Drawing Sheet

FIGURE 1

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 38 NUCLEOTIDES
      (B) TYPE: NUCLEIC ACID SEQUENCE
      (C) STRANDEDNESS: SINGLE STRANDED
      (D) TOPOLOGY: LINEAR    (ii) MOLECULE TYPE: DNA PROBE
      (A) DESCRIPTION: THIS SEQUENCE IS USEFUL AS A DNA PROBE OR AS
         AN RNA PROBE FOR THE SPECIFIC DETECTION OF UREAPLSAMA
         UREALYTICUM 16S RIBOSOMAL RNA.

(ix) FEATURE:
      (A) NAME/KEY: GTS OLIGO NUMBER 2262

(xi) SEQUENCE DESCRIPTION: SEQ ID NO:1:

CCCGTTCACC ACTAAGCCTA AAAGGCTTCG TTCGATTT                38

(2) INFORMATION FOR SEQ ID NO:2:

(i) SEQUENCE CHARACTERISTICS:
      (A) LENGTH: 49 NUCLEOTIDES
      (B) TYPE: NUCLEIC ACID SEQUENCE
      (C) STRANDEDNESS: SINGLE STRANDED
      (D) TOPOLOGY: LINEAR    (ii) MOLECULE TYPE: DNA PROBE
      (A) DESCRIPTION: THIS SEQUENCE IS USEFUL AS A DNA PROBE OR AS
         AN RNA PROBE FOR THE SPECIFIC DETECTION OF UREAPLSAMA
         UREALYTICUM 16S RIBOSOMAL RNA.

(ix) FEATURE:
      (A) NAME/KEY: GTS OLIGO NUMBER 2256

(xi) SEQUENCE DESCRIPTION: SEQ ID NO:2:

CGCGACTTTC TACATCTTCT CATGCGATAA TAATGCCCTA TGCGGTATT       49

(2) INFORMATION FOR SEQ ID NO:3:

(i) SEQUENCE CHARACTERISTICS:
      (A) LENGTH: 38 NUCLEOTIDES
      (B) TYPE: NUCLEIC ACID SEQUENCE
      (C) STRANDEDNESS: SINGLE STRANDED
      (D) TOPOLOGY: LINEAR    (ii) MOLECULE TYPE: DNA PROBE
      (A) DESCRIPTION: THIS SEQUENCE IS USEFUL AS A DNA PROBE OR AS
         AN RNA PROBE FOR THE SPECIFIC DETECTION OF UREAPLSAMA
         UREALYTICUM 16S RIBOSOMAL RNA.

(ix) FEATURE:
      (A) NAME/KEY: GTS OLIGO NUMBER 2246

(xi) SEQUENCE DESCRIPTION: SEQ ID NO:3:

CTATCTGATA CGTCGCACCC CCATCCAAAA GCGTCGCT                38

(2) INFORMATION FOR SEQ ID NO:4:

(i) SEQUENCE CHARACTERISTICS:
      (A) LENGTH: 37 NUCLEOTIDES
      (B) TYPE: NUCLEIC ACID SEQUENCE
      (C) STRANDEDNESS: SINGLE STRANDED
      (D) TOPOLOGY: LINEAR (ii) MOLECULE TYPE: DNA PROBE
             (A) DESCRIPTION: THIS SEQUENCE IS USEFUL AS A DNA PROBE OR AS
                 AN RNA PROBE FOR THE SPECIFIC DETECTION OF UREAPLSAMA
                 UREALYTICUM 16S RIBOSOMAL RNA.

(ix) FEATURE:
             (A) NAME/KEY: GTS OLIGO NUMBER 2218

(xi) SEQUENCE DESCRIPTION: SEQ ID NO:4:

CTAAAATCAT TTCCTATCTT AGCGTTTCTT CCCATAT                                    37

(2) INFORMATION FOR SEQ ID NO:5:

(i) SEQUENCE CHARACTERISTICS:
             (A) LENGTH: 56 NUCLEOTIDES
             (B) TYPE: NUCLEIC ACID SEQUENCE
             (C) STRANDEDNESS: SINGLE STRANDED
             (D) TOPOLOGY: LINEAR (ii) MOLECULE TYPE: DNA PROBE
             (A) DESCRIPTION: THIS SEQUENCE IS USEFUL AS A DNA PROBE OR
                 AS AN RNA PROBE FOR THE SPECIFIC DETECTION OF UREAPLSAMA
                 UREALYTICUM 16S RIBOSOMAL RNA.

(ix) FEATURE:
             (A) NAME/KEY: GTS OLIGO NUMBER 2271

(xi) SEQUENCE DESCRIPTION: SEQ ID NO:5:

CCTTCCTCTA CCTTGCGGTA GCAGTATCGC TAGAAAAGCA ACTAACGAAA GGGGTT              56

(2) INFORMATION FOR SEQ ID NO:6:

(i) SEQUENCE CHARACTERISTICS:
             (A) LENGTH: 34 NUCLEOTIDES
             (B) TYPE: NUCLEIC ACID SEQUENCE
             (C) STRANDEDNESS: SINGLE STRANDED
             (D) TOPOLOGY: LINEAR (ii) MOLECULE TYPE: DNA PROBE
             (A) DESCRIPTION: THIS SEQUENCE IS USEFUL AS A DNA PROBE OR AS
                 AN RNA PROBE FOR THE SPECIFIC DETECTION OF UREAPLSAMA
                 UREALYTICUM 16S RIBOSOMAL RNA.

(ix) FEATURE:
             (A) NAME/KEY: GTS OLIGO NUMBER 2220

(xi) SEQUENCE DESCRIPTION: SEQ ID NO:6:

TCTGTTTCGC TTCATCTTAC GATTTTGCAG CAGT                                       34

(2) INFORMATION FOR SEQ ID NO:7:

(i) SEQUENCE CHARACTERISTICS:
             (A) LENGTH: 39 NUCLEOTIDES
             (B) TYPE: NUCLEIC ACID SEQUENCE
             (C) STRANDEDNESS: SINGLE STRANDED
             (D) TOPOLOGY: LINEAR (ii) MOLECULE TYPE: DNA PROBE
             (A) DESCRIPTION: THIS SEQUENCE IS USEFUL AS A DNA PROBE OR AS
                 AN RNA PROBE FOR THE SPECIFIC DETECTION OF UREAPLSAMA
                 UREALYTICUM 16S RIBOSOMAL RNA.

(ix) FEATURE:
             (A) NAME/KEY: GTS OLIGO NUMBER 2259

(xi) SEQUENCE DESCRIPTION: SEQ ID NO:7:

CACCGACTCG TTCGAGCCGA CATTTAATGA TGATCGTTT                                  39

(2) INFORMATION FOR SEQ ID NO:8:

(i) SEQUENCE CHARACTERISTICS:

(A) LENGTH: 37 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 16S RIBOSOMAL RNA.

(ix) FEATURE:
        (A) NAME/KEY: GTS OLIGO NUMBER 2227

(xi) SEQUENCE DESCRIPTION: SEQ ID NO:8:

CCAATTTACA TTAGCAGTCT CGTTAAACAA TGTAACT                                37

(2) INFORMATION FOR SEQ ID NO:9:

(i) SEQUENCE CHARACTERISTICS:
        (A) LENGTH: 35 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 16S RIBOSOMAL RNA.

(ix) FEATURE:
        (A) NAME/KEY: GTS OLIGO NUMBER 2219
        (B) LOCATION: PROBE TARGETS THE 16S RRNA OF M. PNEUMONIAE AND
            M.GENITALIUM AND IS INCORPORATED WITHIN A COPENDING
            APPLICATION.

(xi) SEQUENCE DESCRIPTION: SEQ ID NO:9:

CCTCCATTAT GTTTCCATAA CTTTGCCAAG GATGT                                  35

(2) INFORMATION FOR SEQ ID NO:10:

(i) SEQUENCE CHARACTERISTICS:
        (A) LENGTH: 31 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 23S RIBOSOMAL RNA.

(ix) FEATURE:
        (A) NAME/KEY: GTS OLIGO NUMBER 2335

(xi) SEQUENCE DESCRIPTION: SEQ ID NO:10:

CAACCCCTAT CCTCAGATAG GTTTGGCCTG T                                      31

(2) INFORMATION FOR SEQ ID NO:11:

(i) SEQUENCE CHARACTERISTICS:
        (A) LENGTH: 35 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 23S RIBOSOMAL RNA.

(ix) FEATURE:
        (A) NAME/KEY: GTS OLIGO NUMBER 2337

(xi) SEQUENCE DESCRIPTION: SEQ ID NO:11:

TTCTATCCTT TTAACTTCCA TAATGCAAGC CCTAC                                        35

(2) INFORMATION FOR SEQ ID NO:12:

(i) SEQUENCE CHARACTERISTICS:
        (A) LENGTH: 34 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 23S RIBOSOMAL RNA.

(ix) FEATURE:
        (A) NAME/KEY: GTS OLIGO NUMBER 2334

(xi) SEQUENCE DESCRIPTION: SEQ ID NO:12:

TGGTTACAGT TAAATTAGCC CTAGCAGCTT TTCT                                         34

(2) INFORMATION FOR SEQ ID NO:13:

(i) SEQUENCE CHARACTERISTICS:
        (A) LENGTH: 31 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            GENITALIUM 23S RIBOSOMAL RNA.

(ix) FEATURE:
        (A) NAME/KEY: GTS OLIGO NUMBER 2336

(xi) SEQUENCE DESCRIPTION: SEQ ID NO:13:

TAAAAGCTTT GCAATAAATT GCTAACCTCC T                                            31

(2) INFORMATION FOR SEQ ID NO:14:

(i) SEQUENCE CHARACTERISTICS:
        (A) LENGTH: 32 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA
            HOMINIS 16S RIBOSOMAL RNA.

(ix) FEATURE:
        (A) NAME/KEY: GTS OLIGO NUMBER 2191

(xi) SEQUENCE DESCRIPTION: SEQ ID NO:14:

CGCCGCTAGT TATTGCTAAC CTCGCTCGAC AT                                           32

(2) INFORMATION FOR SEQ ID NO:15:

(i) SEQUENCE CHARACTERISTICS:
        (A) LENGTH: 49 NUCLEOTIDES
        (B) TYPE: NUCLEIC ACID SEQUENCE
        (C) STRANDEDNESS: SINGLE STRANDED
        (D) TOPOLOGY: LINEAR (ii) MOLECULE TYPE: DNA PROBE
        (A) DESCRIPTION: THIS SEQUENCE IS USEFUL AS A DNA PROBE OR AS
            AN RNA PROBE FOR THE SPECIFIC DETECTION OF MYCOPLASMA

-continued

```
            HOMINIS 16S RIBOSOMAL RNA.

(ix) FEATURE:
          (A) NAME/KEY: GTS OLIGO NUMBER 2228

(xi) SEQUENCE DESCRIPTION: SEQ ID NO:15:

CCGACAGTCT GCAATCATTT CCTATTGCAA ATGTTCTTCC CTTATAACT                49

(2) INFORMATION FOR SEQ ID NO:16:

(i) SEQUENCE CHARACTERISTICS:
          (A) LENGTH: 39 NUCLEOTIDES
          (B) TYPE: NUCLEIC ACID SEQUENCE
          (C) STRANDEDNESS: SINGLE STRANDED
          (D) TOPOLOGY: LINEAR (ii) MOLECULE TYPE: DNA PROBE
          (A) DESCRIPTION: THIS SEQUENCE IS USEFUL AS A DNA PROBE OR AS
              AN RNA PROBE FOR THE SPECIFIC DETECTION OF MYCOPLASMA
              HOMINIS 16S RIBOSOMAL RNA.

(ix) FEATURE:
          (A) NAME/KEY: GTS OLIGO NUMBER 2260

(xi) SEQUENCE DESCRIPTION: SEQ ID NO:16:

GGCAGTATCT CTAGAGTGCTC AACTTAATGT TAGTAACT                           39

(2) INFORMATION FOR SEQ ID NO:17:

(i) SEQUENCE CHARACTERISTICS:
          (A) LENGTH: 45 NUCLEOTIDES
          (B) TYPE: NUCLEIC ACID SEQUENCE
          (C) STRANDEDNESS: SINGLE STRANDED
          (D) TOPOLOGY: LINEAR (ii) MOLECULE TYPE: DNA PROBE
          (A) DESCRIPTION: THIS SEQUENCE IS USEFUL FOR THE DETECTION OF
              16S RIBOSOMAL RNA OF ALL BACTERIAL SPECIES.

(ix) FEATURE:
          (A) NAME/KEY: GTS OLIGO NUMBER OLIGO 1660

(xi) SEQUENCE DESCRIPTION: SEQ ID NO:17:

CTGCTGCCTC CCGTAGGAGT TTGGGCCGTG TCTCAGTTCC AGTGT                    45
```

NUCLEIC ACID PROBES FOR THE DETECTION OF GENITAL MYCOPLASMAS

This is a divisional of application Ser. No.07/673,661 filed mar. 22, 1991.

FIELD OF THE INVENTION

This invention relates to mycoplasmas associated with the genito-urinary tract, believed to be the cause of nongonococcal urethritis, pelvic inflammatory diseases, septic abortion, and a wide array of diseases of other tissues. More specifically, embodiments of the present invention provide nucleic acid probes and compositions, methods for their use for the specific detection or identification of *Mycoplasma hominis*, *Ureaplasma urealyticum*, and *Mycoplasma genitalium* in clinical and other samples, and packaged components suitable for use as kits.

BACKGROUND OF THE INVENTION

Mycoplasmas are small wall-less bacteria, primarily isolated from animal sources including humans. There are over 70 members of the genus Mycoplasma, and several related genera which are also characterized by small wall-less bacteria; these are Spiroplasma, Acholeplasma, Ureaplasma, Anaeroplasma, and Asteroleplasma. Only a handful of the species within these genera have been found associated with humans-some presumed to be "normal flora", others occasionally pathogenic, and still others always believed to be clinically significant. Among the mycoplasmas known to be pathogenic, *Mycoplasma pneumoniae* is historically the most well studied, it is the major infectious agent of primary atypical pneumonia. Nucleic acid compositions and methods for the detection of *Mycoplasma pneumoniae* and a further mycoplasma pathogen, *Mycoplasma fermentans*, are the subject of two concurrently filed applications U.S. Ser. No. 07/673,686 and U.S. Ser. No. 07/673,687, entitled "Nucleic Acid Probes For The Detection Of Mycoplasma Pneumoniae" and "Nucleic Acid Probes For The Detection Of Mycoplasma Fermentans Or The Aids-Associated Virus-Like Infectious Agent." At least one inventor is common to all these applications and the present application.

Three other mycoplasma species, which can be isolated from the human genito-urinary tract, *Mycoplasma hominis*, *Mycoplasma genitalium* and *Ureaplasma urealyticum*, are somewhat more enigmatic in the clinical implications of the detection of these organisms in the human body. Ureaplasma urealyticum, for example, although it is implicated in significant and serious human morbidity and mortality, may be found in asymptomatic "normal" individuals as well. The three species, *Mycoplasma hominis*, *Mycoplasma genitalium*, and *Ureaplasma urealyticum* will be referred to herein as the genital mycoplasmas.

*Mycoplasma genitalium* was initially isolated from the urethras of two males with nongonococcal urethritis (Tully, et. al., Int. J. Syst. Bacteriol. vol. 33, 1983). Subsequently, *M. genitalium* was isolated from the human respiratory tract, in co-culture with *Mycoplasma pneumoniae* (Baseman, et. al., J. Clinical Micro. vol.26, 1988). However, studies have shown (for example Hooton, et.al., Lancet, 1988) that *M. genitalium* plays a role in at least some of the cases of acute urethritis, particularly in homosexual males. It is an aspect of the present invention to describe methods for the design and manufacture of probes specific for the detection of *Mycoplasma genitalium*. Nucleic acid probes which recognize both *M. genitalium* and *Mycoplasma pneumoniae*, evolutionary close relatives, are described in an application filed concurrently.

*Mycoplasma hominis* has been implicated as a causative agent of salpingitis, amnionitis, nonspecific vaginitis, and postpartum septic fever. *Mycoplasma hominis* can be isolated from a significant number of asymptomatic women. It is an aspect of the present invention to describe methods for the design and manufacture of probes specific for the detection of *Mycoplasma hominis*.

*Ureaplasma urealyticum* has been implicated in nongonococcal urethritis, chorioamnionitis, premature delivery, and perinatal morbidity and mortality. Some clinical investigators estimate that the etiological agency of nongonococcal urethritis (NGU) by *Ureaplasma urealyticum* may approach the same levels as that of *Chlamydia trachomatis*. As much as 40% of acute NGU may be caused by ureaplasma (Bowie, Urological Clinics of North America, vol. 11, 1984). This translates to approximately 3–4 million United States cases per year. Like *Mycoplasma hominis*, *Ureaplasma urealyticum* can be isolated from a significant number of both male and female asymptomatic individuals. There are at least 15 serotypes of *Ureaplasma urealyticum*. The combination of serotype, numerical prevalence and other factors that contribute to ureaplasma pathogenesis is, at present, totally unknown. It is an aspect of the present invention to describe methods for the design and manufacture of probes specific for the detection of *Ureaplasma urealyticum*.

The mycoplasmas, such as those described above, are fastidious organisms, requiring complex culture media containing peptone, yeast extract, expensive animal sera, and sterol. Growth is relatively slow and reaches low cell densities compared to most bacteria. In addition, atmospheric conditions for cell growth require the addition of carbon dioxide. For these reasons, many clinical laboratories are unable to perform culture isolation of mycoplasmas, and consequently are left with no real ability to diagnose the presence of these important pathogenic bacteria. Given that mycoplasmas lack cell walls, antibiotics that target the bacterial cell wall, such as penicillin, have no anti-mycoplasma activity. Consequently, it is of importance for a physician to make a diagnosis of the presence of one or more of these bacteria, particularly if the clinical presentation is predictive, and prescribe the appropriate antibiotic.

Ribosomes are of profound importance to all organisms. Ribosomes serve as the only known means of translating genetic information into cellular proteins, the main structural and catalytic elements of life. A clear manifestation of this importance is the observation that all cells have ribosomes.

Bacterial ribosomes contain three distinct RNA molecules which, at least in *Escherichia coli*, are referred to as 5S, 16S and 23S rRNAs. In eukaryotic organisms, there are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacterium, including the mycoplasmas, and this convention will be continued herein. The probes of the present invention target the 16S and 23S rRNA molecules of the genital mycoplasmas.

Hybridization is a process by which, under appropriate reaction conditions, two partially or completely complementary strands of nucleic acid are allowed to come together In an antiparallel fashion (one oriented 5' to 3', the other 3' to 5') to form a double-stranded nucleic acid with specific and stable hydrogen bonds, following explicit rules pertaining to which nucleic acid bases may pair with one another.

As used herein, probe(s) refer to synthetic or biologically produced nucleic acids (DNA or RNA) which, by design or selection, contain specific nucleotide sequences that allow them to hybridize under hybridization conditions, specifically and preferentially, to target nucleic acid sequences. The term "preferentially" is used In a relative sense, one hybridization reaction product is more stable than another under identical conditions. Under some conditions, a hybridization reaction product may be formed with respect to one target, but not to another potential binding partner. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescein, biotin, etc.), to facilitate detection (e.g. chemiluminescent, fluorescent agents and radioactive agents) or to facilitate their capture onto a solid support (e.g., homopolymer "tails"). Such modifications are elaborations on the basic probe function which is the probe's ability to usefully discriminate between target and non-target organisms in a hybridization assay.

A minimum of ten nucleotides are necessary in order to statistically obtain specificity and form stable hybridization products. A maximum of 250 nucleotides represents an upper limit of sequences in which reaction parameters can be adjusted to determine mismatched sequences and preferential hybridization.

Hybridization conditions are defined by the base composition of the probe/target duplex, as well as by the level and geometry of mispairing between the two nucleic acids. Normal hybridization conditions for nucleic acid of 10 to 250 bases are a temperature of approximately 60° C. in the presence of 1.08 M sodium chloride, 60 mM sodium phosphate, and 6 mM ethylenediamine tetraacetic acid (pH of 7.4).

Reaction parameters which are commonly adjusted include concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

Kohne et.al. (*Biophysical Journal* 8:1104–1118, 1968) discuss one method for preparing probes to rRNA sequences. However, Kohne et.al. do not provide the teaching necessary to make probes to detect the three species of genital mycoplasmas.

Pace and Campbell (*Journal of Bacteriology* 107:543–547, 1971) discuss the homology of ribosomal ribonucleic acids from diverse bacterial species and a hybridization method for quantitating such homology levels. Similarly, Sogin, Sogin and Woese (*Journal of Molecular Evolution* 1:173–184, 1972) discuss the theoretical and practical aspects of using primary structural characterization of different ribosomal RNA molecules for evaluating phylogenetic relationships. Fox, Pechman and Woese (*International Journal of Systematic Bacteriology* 27:44–57, 1977) discuss the comparative cataloging of 16S ribosomal RNAs as an approach to prokaryotic systematics. Separately, or together, Kohne et al, Pace and Campbell, Sogin, Sogin and Woese, and Fox, Pechman and Woese fail to provide specific probes useful in assays for detecting the presence and abundance of genital mycoplasmas.

Hogan, et.al. (International Patent Application, Publication Number WO 88/03957) describe five probes for the specific detection of *Mycoplasma pneumoniae*. However, Hogan et.al. do not describe probes to the specific three genital mycoplasma species.

Woese, Maniloff, Zablen (*Proc. Natl. Acad. Sci. USA* vol. 77, 1980) examined the partial sequences of selected mycoplasma 16S rRNA, and define the concept of mycoplasma sequence "signature". However, Woese et.al. fail to teach the art of probe design. Woese et.al. do not discuss *M. genitalium, M. hominis,* or *Ureaplasma urealyticum*.

Rogers, et.al. (*Proc. Natl. Acad. Sci.*, USA, vol. 82, 1985) discuss sequences of 5S rRNA. However, Rogers et.al. fail to teach the art of probe design. Rogers et.al. do not mention *M. genitalium* or *M. hominis*.

Weisburg, et.al. (*Jnl. Bacteriology*, vol.171, 1989) discuss 16S rRNA sequences of *Ureaplasma urealyticum* and *M. hominis*. However, Weisburg et.al. do not discuss or teach mycoplasma probe design.

Hyman, et al. (Hymen, et al., Jnl. Clin. Micro., vol. 25, 1987) and Jensen, et al. (Jensen, et al., Jnl. Clin. Micro. vol 29, 1991) discuss detection of *Mycoplasma genitalium* using polymerase chain reaction (PCR). Both papers fail to teach. non-PCR assays with respect to the utility of the sequences of mycoplasma rRNA or rDNA.

SUMMARY OF THE INVENTION

The present invention features nucleic acid compositions and composition sets, and methods for their use for the specific detection or identification of *Mycoplasma hominis, Ureaplasma urealyticum,* and *Mycoplasma genitalium*. One embodiment of the present invention features, as a composition of matter, a nucleic acid having approximately 10 to 250 nucleotides capable of hybridizing to rRNA or rDNA of pathogenic mycoplasma bacteria associated with human urinary tract and genital areas, in preference to rRNA or rDNA of nonmycoplasma bacteria in humans. The nucleic acid composition is useful for detecting *Mycoplasma hominis, Ureaplasma urealyticum* and *Mycoplasma genitalium*.

The nucleic acid composition are complementary to or homologous with a region of rRNA or rDNA selected from the group of regions consisting of positions 50 to 100, 425 to 485, or 1100 to 1150 of the *Mycoplasma hominis* 16S rRNA, positions 50 to 100, 150 to 250, 425 to 485, 800 to 850, 1090 to 1160, and 1220 to 1260 of the *Ureaplasma urealyticum* 16S rRNA, positions 1110 to 1160 of the *Mycoplasma genitalium* 16S rRNA, and positions 260 to 330, 1590 to 1630, and 1850 to 1900 of the *Mycoplasma genitalium* 23S rRNA. Ass such numerical designations are nucleotide positions counted from the 5' end of the RNA molecule, a convention known to those skilled in the art.

Preferably, the nucleic acid composition is complementary to at least 90° of a sequence comprising any ten consecutive nucleotides within a nucleic acid sequence selected from the group consisting of probes 2262 (Sequence No. 1), 2256 (Sequence No. 2), 2246 (Sequence No. 3), 2218 (Sequence No. 4), 2271 (Sequence No. 5), 2220 (Sequence No. 6), 2259 (Sequence No. 7), 2227 (Sequence No. 8), 2219 (Sequence No. 9), 2335 (Sequence No. 10), 2337 (Sequence No. 11), 2334 (Sequence No. 12), 2336

(Sequence No. 13), 2191 (Sequence No. 14), 2228 (Sequence No. 15), and 2260 (Sequence No. 16).

A further embodiment of the present invention includes a nucleic acid which is homologous to at least 90% of a sequence comprising any ten consecutive nucleotides within the sequences selected from the group consisting of probes 2262 (Sequence No. 1), 2256 (Sequence No. 2), 2246 (Sequence No. 3), 2218 (Sequence No. 4), 2271 (Sequence No. 5), 2220 (Sequence No. 6), 2259 (Sequence No. 7), 2227 (Sequence No. 8), 2219 (Sequence No. 9), 2335 (Sequence No. 10), 2337 (Sequence No. 11), 2334 (Sequence No. 12), 2336 (Sequence No. 13), 2191 (Sequence No. 14), 2228 (Sequence No. 15), and 2260 (Sequence No. 16).

One embodiment of the present invention features as an article of manufacture a set of at least two nucleic acid compositions. Each nucleic acid composition having approximately 10 to 250 nucleotides capable of hybridizing preferentially to rRNA or RDNA of *Mycoplasma hominis, Mreaplasma urealyticum* and *Mycoplasma genitalium*. Each nucleic acid is complementary to or homologous with at least 90%/ of a sequence comprising any ten consecutive nucleotides within the sequences selected from the group defined by probes consisting of 2262 (Sequence No. 1), 2256 (Sequence No. 2); 2246 (Sequence No. 3), 2218 (Sequence No. 4), 2271 (Sequence No. 5), 2220 (Sequence No. 6), 2259 (Sequence No. 7), 2227 (Sequence No. 8), 2219 (Sequence No. 9), 2335 (Sequence No. 10), 2337 (Sequence No. 11), 2334 Sequence No. 12), 2336 (Sequence No. 13), 2191 (Sequence No. 14), 2228 (Sequence No. 15), and 2260 (Sequence No. 16).

Probe sets suited for detecting *Ureaplasma urealyticum* includes probe 2262 (Sequence No. 1) and probe 2256 (Sequence No. 2); probe 2246 (Sequence No. 3) and probe 2218 (Sequence No. 4); probe 2259 (Sequence No. 7) and probe 2271 (Sequence No. 5); probe 2271 (Sequence No. 5) and probe 2220 (Sequence No. 6); and their complements.

Probe sets that are suited for detecting *Mycoplasma hominis* includes probe 2191 (Sequence No. 14) and probe 2228 (Sequence No. 15); probe 2228 (Sequence No. 15) and probe 2260 (Sequence No. 16); probe 2191 (Sequence No. 14) and probe 2260 (Sequence No. 16); and their complements.

Probe sets which are suitable for detecting *Mycoplasma genitalium* include probe sets 2227 (Sequence No. 8) and probe 2219 (Sequence No. 9); probe 2335 (Sequence No. 10) and probe 2337 (Sequence No. 11); probe 2335 (Sequence No. 10) and probe 2334 (Sequence No. 12); probe 2334 (Sequence No. 12); and probe 2336 (Sequence No. 13); and their complements. The probe 2227 (Sequence No. 8) and probe 2219 (Sequence No. 9) are capable of hybridization to the rRNA of the 16S ribosomal subunit. The probe sets probe 2335 (Sequence No. 10) and probe 2337 (Sequence No. 11); probe 2335 (Sequence No. 10) and probe 2334 (Sequence No. 12); probe 2334 (Sequence No. 12) and probe 2336 (Sequence No. 13) are capable of hybridizing to the 23S ribosomal subunit.

Embodiments of the present invention are also directed to methods for detecting *Mycoplasma hominis, Ureaplasma urealyticum*, and *Mycoplasma genitalium*. The method includes contacting a sample potentially containing the microorganisms with at least one nucleic acid composition having 10 to 250 nucleotides capable of hybridizing preferentially to rRNA or rDNA of *Mycoplasma hominis, Ureaplasma urealyticum*, and *Mycoplasma genitalium*. The base sequences, under conditions that allow the nucleic acid composition to hybridize, hybridize preferentially to rRNA or rDNA of the mycoplasma organism. Upon imposition of hybridization conditions on the sample, a hybridization product is formed in the presence of target. The detection of the hybridization product is an indication of the presence of the mycoplasma.

The method of the present invention features nucleic acid compositions which are complementary to or homologous with at least 90% of a 10 nucleotide sequence within the sequences selected from the group defined by probes consisting of 2219 (Sequence No. 9), 2262 (Sequence No. 1), 2256 (Sequence No. 2), 2246 (Sequence No. 3), 2218 (Sequence No. 4), 2271 (Sequence No. 5), 2220 (Sequence No. 6), 2259 (Sequence No. 7), 2227 (Sequence No. 8), 2335 (Sequence No. 10), 2337 (Sequence No. 11), 2334 (Sequence No. 12), 2336 (Sequence No. 13), 2191 (Sequence No. 14), 2228 (Sequence No. 15) and 2260 (Sequence No. 16).

Embodiments of the present invention also feature a method employing a first nucleic acid composition and a second nucleic acid composition. Each composition of different sequences, and each is complementary to or homologous with at least 90% of 10 nucleic acid sequences within the group of sequences defined by probes consisting of 2219 (Sequence No. 9), 2262 (Sequence No. 1), 2256 (Sequence No. 2), 2246 (Sequence No. 3), 2218 (Sequence No. 4), 2271 (Sequence No. 5), 2220 (Sequence No. 6), 2259 (Sequence No. 7), 2227 (Sequence No. 8), 2335 (Sequence No. 10), 2337 (Sequence No. 11), 2334 (Sequence No. 12), 2336 (Sequence No. 13), 2191 (Sequence No. 14), 2228 (Sequence No. 15) and 2260 (Sequence No. 16). Preferably the sequences of sets are probe 2262 (Sequence No. 1) and 2256 (Sequence No. 2); probe 2246 (Sequence No. 3) and probe 2218 (Sequence No. 4); probe 2259 (Sequence No. 7) and probe 2271 (Sequence No. 5); probe 2271 (Sequence No. 5) and probe 2220 (Sequence No. 6); probe 2191 (Sequence No. 14) and probe 2228 (Sequence No. 15); probe 2228 (Sequence No. 15) and probe 2260 (Sequence No. 16); probe 2191 (Sequence No. 14) and probe 2260 (Sequence No. 16); probe 2227 (Sequence No. 8) and probe 2219 (Sequence No. 9); probe 2335 (Sequence No. 10) and probe 2337 (Sequence No. 11); probe 2335 (Sequence No. 10) and probe 2334 (Sequence No. 12); and probe 2334 (Sequence No. 12) and probe 2336 (Sequence No. 13).

Individuals skilled in the art will recognize that the probe compositions of the present invention can be packaged with suitable instructions for their use as kits for detecting the presence of one or more of the organisms *Mycoplasma hominis, Ureaplasma urealyticum* and *Mycoplasma genitalium*.

The nucleic acid compositions and the methods of the present invention provide the basis for nucleic acid hybridization assay for the specific detection of three of the presumptive etiological agents of nongonococcal urethritis, septic abortion, pelvic inflammatory disease, postpartum fever, in clinical samples such as genital swabs, genital lavage, sputum, throat swabs, blood, urine, cerebrospinal fluid, skin, biopsy, saliva, synovial fluid, bronchial wash, bronchial lavage, or other tissue or fluid samples from human patients or veterinary subjects. The nucleic acid compositions of the present invention also form the basis for confirmation of the presence of the genital mycoplasmas in liquid or semi-solid in vitro culture.

Embodiments of the present invention feature nucleic acid compositions capable of hybridizing to rRNA. Ribosomal RNAs constitute a significant component of cellular mass. Although estimates of cellular ribosome content vary, actively growing bacterial cells may contain upwards of 10,000 ribosomes per cell, and therefore 10,000 copies of each of the rRNAs present in a 1:1:1 stoichiometry in ribosomes. In contrast, other potential cellular target molecules such as genes or RNA transcripts thereof, are less ideal since they are present in much lower abundance. However, due to the close similarity of many organisms with which you may wish to distinguish mycoplasma species from, there can be no assurance that nucleic acid compositions can indeed be formulated which hybridize preferentially to the rRNA and RDNA of *Mycoplasma hominis, Ureaplasma urealyticum* and *Mycoplasma genitalium*.

The discovery that probes could be generated with the extraordinary inclusivity and exclusivity characteristics of those of the present invention with respect to the detection of genital mycoplasma isolates, without necessarily incurring cross-reactivity between these species, or toward other bacterial taxa, except as documented, was unpredictable and unexpected.

BRIEF DESCRIPTION OF THE TABLES AND FIGURE

A further understanding of the principles and aspects of the present invention may be made by reference to the tables and FIG. 1 described briefly below.

Table 1 describes the physical structure of the probes.

Tables 2, 3, 4, and 5 display the hybridization behavior of the probes toward a panel of clinically and environmentally representative mycoplasma species.

Table 6 sets forth the 16S rRNA sequences of *Mycoplasma hominis M. genitalium*, and *U. urealyticum* and the 23S rRNA sequences of *Mycoplasma genitalium*.

DETAILED DESCRIPTION OF THE INVENTION AND BEST MODE

Preferred embodiments of the present invention will be discussed with respect to nucleic acid compositions having particular utility as probes for *Mycoplasma hominis Ureaplasma urealyticum* and *M. Mycoplasma genitalium*. The detailed discussion will feature probe development strategy, dot blot analysis, sandwich hybridization assays, instrument hybridization and amplification.

I. Probe Development Strategy

The first step taken in the development of the probes of the present invention involved identification of regions of the 16S rRNA and 23S rRNA which potentially could serve as target sites for specific nucleic acid probes with the desired sensitivity. To obtain the desired sensitivity a search began for probe targets unique to *Mycoplasma hominis, Ureaplasma urealyticum*, and *Mycoplasma genitalium*.

Precise alignments of mycoplasma 16S and 23S rRNA sequences were developed. The essentially complete 16S rRNA and 23S rRNA sequences from *Mycoplasma genitalium* were determined. The 16S rRNA sequences from *Ureaplasma urealyticum* and *Mycoplasma hominis* are those of Weisburg, et.al. (Journal of Bacteriology, vol. 171, 1989) and are available through GENBANK accession numbers M23935 and M24473.

The nucleotide sequences from *M. genitalium* were determined by standard laboratory protocols well known to those skilled in the art of probe design. By way of example, the sequences can be determined from plasmid clones which were generated by ligating polymerase chain reaction products from 16S rDNA and 23S rDNA into restriction digested plasmid vectors.

The mycoplasma sequences were aligned with homologous sequences of other mycoplasma and nonmycoplasma ribosomal RNA sequences in order to identify regions of interesting variation. The regions of interesting variation are identified with each probe construct of Table 1.

In addition to the consideration of the target sequences of *M. hominis, M. genitalium*, and *U. urealyticum*, the exclusion from hybridization of other mycoplasmas, and other genital and pathogenic organisms was considered. Probe regions were compared to 16S rRNA sequences of the following organisms (GenBank accession numbers shown in Weisburg, et.al., Jnl. Bacteriology, vol. 171, 1989): *M. agalactiae, M. arginini, M. arthritidis, M. bovigenitalium, M. californicum, M. capricolum, M. ellychiae, M. melaleucum, M. fermentans, M. gallisepticum. M. hyopneumonia, M. hyorhinis, M. iowae, M. Iipophilum, M. mobile, M. muris, M. mycoides, M. neurolyticum M. orale, M. pirum. M. pneumoiae, M. pulmonis, M. putrefaciens, M. salivarium, M. sualvi*, ten *Spiroplasma* species' sequences, four *Acholeplasma* species' sequences, four *Anaeroplasma* species' sequences, and one *Asteroleplasma* sequence.

For consideration of other microorganisms capable of causing similar types of genital morbidity, rRNA sequences from several Candida yeasts, *Neisseria gonorrhoeae, Chlamydia trachomatis, Treponema pallidum*, and numerous other species were utilized, the majority of which are available from sequence compilation such as GenBank. Individuals skilled in the art will recognize that sequences of interest as probes can be compared to other organisms as well.

Sixteen probes—designed, synthesized, and tested—are described in Table 1. One probe, probe 2219, is the subject of a copending U.S. Ser. No. 07/673,686, entitled "Nucleic Acid Probes for the Detection of Mycoplasma Pneumoniae." Seven probes show interesting specificity toward *Ureaplasma urealyticum* 16S rRNA. Three probes show interesting specificity toward *Mycoplasma hominis* 16S rRNA. One probe shows interesting specificity toward *Mycoplasma genitalium* 16S rRNA. And, four probes show interesting specificity toward *Mycoplasma genitalium* 23S rRNA. Probes which recognize both *Mycoplasma genitalium* and *Mycoplasma pneumoniae* are described in an application concurrently filed herewith in which the inventive entity is Weisburg and Pelletier.

DESCRIPTION OF THE PROBES

The probe selection strategy yielded sixteen nucleic acid compositions useful for hybridization to the genital mycoplasmas in clinical or other samples. The specific behavior of the probes in one format is documented in Tables 2, 3, 4, and 5.

Referring now to said Tables, the three representative strains of *M. genitalium* represent a selection from the National Institute of Allergy and Infectious Disease's Mycoplasma Section. The five representative *Mycoplasma hominis* strains and all 15 serovars of *Ureaplasma urealyticum* are a representative collection from the University of Alabama at Birmingham mycoplasma collection. Additional species of bacteria and a few fungi were added to the panel in order to represent the breadth of known bacterial taxa.

Specific strains of species are represented by the application of purified, denatured RNA to a membrane and probe hybridization thereto. Probes were synthesized by standard methods and chemistries well known to those skilled in the art, $^{32}$Phosphorous labelled, hybridized to panels under standard conditions, at 60° C. and autoradiographically evaluated.

In Table 2, hybridization is expressed as either "+"OF "−". Positive hybridization is evaluated based on autoradiographic detection of a signal after three hours exposure. The probes in this panel were evaluated in this manner because cultures of *Ureaplasma urealyticum* seldom achieve cell density greater than 1 million cells per milliliter. In order to normalize the signals generated by hybridization of the ureaplasma probes to the *Ureaplasma urealyticum* targets, hybridization signal was compared to that of a probe known to hybridize to all bacterial species (co-pending U.S. Ser. No. 359,158; read Probe 1660. If signals from Probe 1660 were very weak, the candidate ureaplasma probe's signal was "normalized" accordingly. All of the Ureaplasma urealyticum "+" designations would accordingly be considered "+++" or "++++" if the amount of nucleic acid spotted for each of the strains were adjusted so as to give equal signals to the control probe, Probe 1660.

In Tables 3, 4, and 5 "++++" represents strongest hybridization signal after three hours exposure, with slightly lighter signal represented by "+++," diminishing to "++," then "+." "−" is virtually absent, and "" is indicative of no hybridization of probe to target.

The specific behaviors of the aforementioned probes are dependent to a significant extent on the assay format in which they are employed. Conversely, the assay format will dictate certain of the optimal features of particular probes. The "essence" of the probes of the invention is not to be construed as restricted to the specific string of nucleotides In the named probes. For example, the length of these particular oligonucleotides was optimized for use in the dot blot assay and sandwich assays. It is well known to those skilled in the art that optimal probe length will be a function of the stringency of the hybridization conditions chosen and hence the length of the probes disclosed herein may be altered accordingly. Generally, in order to create stability and obtain sufficient exclusivity and inclusivity, probe sequences comprise at least 10 nucleotides. Probe sequences rarely exceed 250 nucleotides. The longer nucleic acids are more difficult to control to obtain necessary exclusivity and inclusivity.

In considering sets comprised of more than one probe, it is desirable that all probes behave in a compatible manner in any particular format in which they are employed. Thus, the exact length of a particular probe will to a certain extent reflect its specific intended use.

The nucleic acids of the present invention circumscribe sequences which can be employed as oligonucleotide probes, or could be incorporated into larger polynucleotides of either ribonucleic acid or deoxyribonucleic acid. Sequences complementary to the probe sequences described herein can be used as probes to rRNA genes. The preferred probe sequences or their complements can be employed as chain elongation initiators for polymerase chain reaction, sequencing or other applications.

The physical description of the probes can be ascertained with reference to the incorporated Tables I and 2. The abbreviations for nucleotides—G, A, C, and T—as well as polarity indicated by 5' and 3' are standard designations well known to one skilled in the art.

The experimental specificity of the preferred probes, as described in Example 1 is summarized in Tables 2, 3, 4, and 5. The specificity is empirical and as stated previously dependent on the format in which they are employed.

EXAMPLES

Example 1

Dot-Blot Analysis of Probe Hybridization Behavior

Dot-blot analysis, in accordance with well known procedures, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target will exhibit a higher level of hybridization than probes containing less complementarity.

Nucleic acid sequences of the present invention were tested In a dot-blot format. One hundred nanogram of RNA, except Ureaplasma, as indicated, purified by phenol extraction and ethanol precipitation was denatured and spotted on a nylon membrane. Probes were isotopically labelled with the addition of a $^{32}$Phosphorous moiety to the 5' end of the oligonucleotide. Hybridization of probes occurred, at a temperature of 60° C. in the presence of 1.08 M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals was evaluated after three hours of exposure.

Tables 2, 3, 4, and 5 summarize the behavior of the probes as employed in the present example, and document the specificity summarized above.

Example 2

Dual Probe Hybridization

Figure 1:
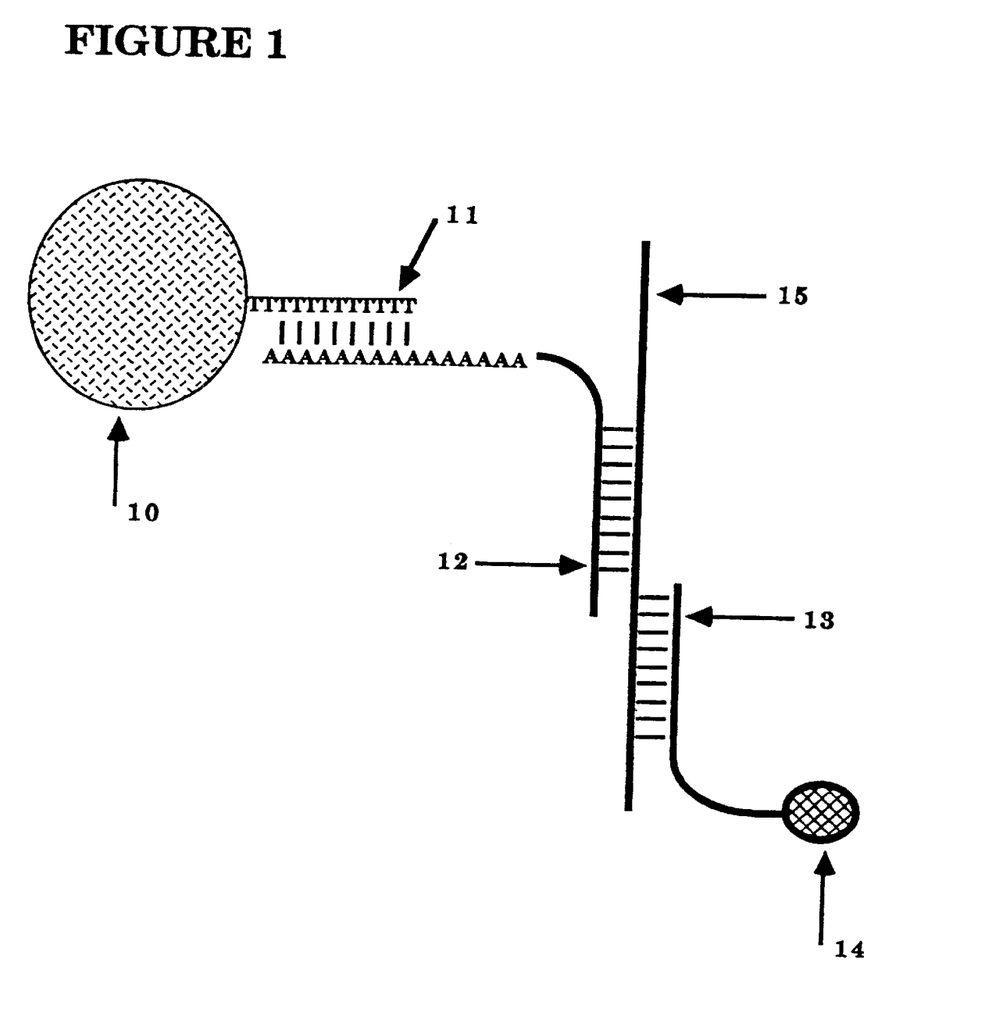
FIG. 1 is a schematic representation of a dual probe capture/detector assay.

One embodiment of the present invention includes the use of probes in a "sandwich" hybridization scheme. Turning now to FIG. 1, the sandwich hybridization scheme employs a capture probe 12 and detector probe 13. The capture probe 12 is a bifunctional polynucleotide manufactured by adding a homopolymeric 3' tail to probe sequences with high target specificity. The tail would, in turn, hybridize to the complimentary homopolymer 11 on a solid surface 10, such as a glass bead or a filter disc. Hybridization of the capture probe 12 to its target 15, in this case mycoplasma rRNA, forms a target-probe complex with the solid support 10. The detector probe 13, is capable of binding to target with some degree of specificity, would be part of a detection scheme relying on radioactivity, fluorescence, chemiluminescence, color, and the like. Detector probe 13 has a detection moiety 14 which would report the presence of the entire hybridization complex. The detector probe 13 could potentially be incorporated as an RNA sequence into an amplifiable Q-beta midivariant as described by Kramer and Lizardi (Nature, vol. 339, 1989).

Example 3

Clinical Diagnosis of Genital Mycoplasma Infection

A clinical sample, such as a swab, urine, or lavage is processed so as to liberate the total nucleic acid content. The sample, containing disrupted mycoplasmas is incubated in the presence of capture probe, detector probe, and magnetic particle beads which have been derivatized with oligo-Thymidine—as in Example 2—in a chaotropic buffer such as guanidinium isothiocyanate.

If target molecules, *Mycoplasma genitalium* 16S or 23S rRNA, *Ureaplasma urealyticum* 16S rRNA, or *Mycoplasma hominis* 16S rRNA (depending on which probe sets are employed) are present, a Bead+Capture Probe+Target+Detector Probe hybridization complex is formed, as in FIG. 1. The presence of a magnet near the bottom of the reaction tube will cause the magnetic particle now carrying the hybridization complex to adhere to the side of the tube enabling removal of the sample matrix, unbound probe, etc. Repeated rehydration and denaturation of the bead+probe+ target complex would enable significant background reduction (as described in U.S. Ser. No. 922,155, Collins, 1986). In this example, final detection could entail spotting the beads on membrane and assaying by autoradiography. Alternatively, the detector probe could be an amplifiable midivariant probe as described In Example 2.

For this particular assay, the following capture and detector probes are examples of preferred pairs:

(1) Ureaplasma urealyticum 16S rRNA Probe 2262 (Sequence No. 1)+Probe 2256 (Sequence No. 2) Probe 2246 (Sequence No. 3)+Probe 2218 (Sequence No. 4) Probe 2259 (Sequence No. 7)+Probe 2271 (Sequence No. 5) Probe 2271 (Sequence No. 5)+Probe 2220 (Sequence No. 6)

(2) Mycoplasma hominis 16S rRNA Probe 2191 (Sequence No. 14)+Probe 2228 (Sequence No. 15) Probe 2228 (Sequence No. 15)+Probe 2260 (Sequence No. 16) Probe 2191 (Sequence No. 14)+Probe 2260 (Sequence No. 16)

(3) Mycoplasma genitalium 16S rRNA Probe 2227 (Sequence No. 8)+Probe 2219 (Sequence No. 9)

(4) Mycoplasma genitalium 23S rRNA Probe 2335 (Sequence No. 10)+Probe 2337 (Sequence No. 11) Probe 2335 (Sequence No. 10)+Probe 2334 (Sequence No. 12) Probe 2334 (Sequence No. 12)+Probe 2336 (Sequence No. 13)

Example 4

Clinical Diagnosis of *M. Hominis, M. Genitalium,* or *U. Urealyticum* Infection from Human Sample Employing Polymerase Chain Reaction Amplification of Mycoplasma rDNA Sample processing is designed so as to yield DNA. One of the probes described herein is used in conjunction with the antiparallel complement of one of the probes described herein to enzymatically amplify a segment of *M. genitalium,* *M. hominis, U. urealyticum* encoding mycoplasma rRNA in a polymerase chain reaction. Resultant material can then be assayed in a "sandwich" hybridization (Example 2) with any of the probes described herein. The polymerase chain reaction can, itself, be made either highly specific by employing probe/primers described herein, or the reaction can be made more general using probes such as those described in co-pending U.S. Ser. No. 359,158, and then identifying the amplification product as a genital mycoplasma as described in Example 2.

Example 5

In situ Hybridization as a Cytological Stain

The probes of the present invention could also be employed as cytological staining reagents. For example, a genital swab is applied to a microscope slide. After appropriate fixation and lysis, hybridization of probes is carried out in situ. In this example, mycoplasmas could be visualized in a specimen by fluorescently labeling Probes 2227 (Sequence No. 8), 2260 (Sequence No. 16), and 2271 (Sequence No. 5), and examining the slide using a fluorescent microscope, looking for small fluorescent bodies.

Example 6

Confirmation of Presumptive Mycoplasma Species Identification Following Culture

Following a standard cultivation step for *Mycoplasma hominis, M. genitalium,* or *Ureaplasma urealyticum,* for example on H-agar plates, SP-6 broth, 10B broth, or A8 agar, a colony or liquid culture is tested for the presence of one of the genital mycoplasmas by employing sandwich hybridization assays as described in Examples 2 and 3. A pure culture is not necessary.

Thus, the present invention features nucleic acid compositions which are suitable for use in detecting the presence of *Mycoplasma hominis, Ureaplasma urealyticum,* and *Mycoplasma genitalium.* Individuals skilled in the art will readily recognize that probes, reagents and compositions necessary to test a sample for the presence of one of these organisms may be packaged in suitable containment vessels assembled into a kit. Such probes, reagents and compositions of the kit would be used to test a sample for one or more of the organisms specified above.

While preferred embodiments of the present invention have been illustrated and described, it is understood that the present invention is capable of variation and modification and, therefore should not be limited to the precise details set forth, but should include such changes and alterations that fall within the purview of the following claims.

TABLE 1

*Ureaplasma urealyticum* 16S rRNA Probes

| | |
|---|---|
| Ureaplasma urealyticum Probe 2262 (38mer 47% G + C)<br>5'-CCC GTT CAC CAC TAA GCC TAA AAG GCT CGT TCG GAT TT-3' | SEQ ID NO: 1 |
| Ureaplasma urealyticum Probe 2256 (49mer 43% G + C)<br>5'-CGC GAC TTT CTA CAT CTT CTC ATG CGA TAA TAA TGC CCT ATG CGG TAT T-3' | SEQ ID NO: 2 |

TABLE 1-continued

| | |
|---|---|
| *Ureaplasma urealyticum* Probe 2246 (38mer 55% G + C)<br>5'-CTA TCT GAT ACG TCG CAC CCC CAT CCA AAA GCG TCG<br>CT-3' | SEQ ID NO: 3 |
| *Ureaplasma urealyticum* Probe 2218 (37mer 33% G + C)<br>5'-CTA AAA TCA TTT CCT ATC TTA GCG TTT CTT CCC ATA T-3' | SEQ ID NO: 4 |
| *Ureaplasma urealyticum* Probe 2271 (56mer 50% G + C)<br>5'-*CCT TCC TCT ACC TTG CGG TAG CAG TAT CGC TAG*<br>     *AAA AGC AAC TAA CGA AAG GCC TT*-3' | SEQ ID NO: 5 |
| *Ureaplasma urealyticum* Probe 2220 (34mer 42% G + C)<br>5'-TCT GTT TCG CTT CAT CTT ACG ATT TTG CAG CAG T-3' | SEQ ID NO: 6 |
| *Ureaplasma urealyticum* Probe 2259 (39mer 46% G + C)<br>5'-CAC CGA CTC GTT CGA GCC GAC ATT TAA TGA TGA TCG TTT-3' | SEQ ID NO: 7 |

*Mycoplasma genitalium* 16S rRNA Probes

| | |
|---|---|
| *Mycoplasma genitalcum* Probe 2227 (37mer 36% G + C)<br>5'-CCA ATT TAC ATT AGC AGT CTC GTT AAA CAA TGT AAC T-3' | SEQ ID NO: 8 |
| *M. pneumoniae* + *M. genitalium* Probe 2219<br>(35mer 40% G + C)<br>5'-CCT CCA TTA TGT TTC CAT AAC TTT GCC AAG GAT GT-3'<br>(Probe 2219 is incorporated within a copending<br>application filed concurrently herewith.) | SEQ ID NO: 9 |

*Mycoplasma genitalium* 23S rRNA Probes

| | |
|---|---|
| *Mycoplasma genitalium* Probe 2335 (31mer 52% G + C)<br>5'-CAA CCC CTA TCC TCA GAT AGG TTT GGC CTG T-3' | SEQ ID NO: 10 |
| *Mycoplasma genitalium* Probe 2337 (35mer 37% G + C)<br>5'-TTC TAT CCT TTT AAC TTC CAT AAT GCA AGC CCT AC-3' | SEQ ID NO: 11 |
| *Mycoplasma genitalium* Probe 2334 (34mer 38% G + C)<br>5'-TGG TTA CAG TTA AAT TAG CCC TAG CAG CTT TTC T-3' | SEQ ID NO: 12 |
| *Mycoplasma genitalium* Probe 2336 (31mer 32% G + C)<br>5'-TAA AAG CTT TGC AAT AAA TTG CTA ACC TCC T-3' | SEQ ID NO: 13 |

*Mycoplasma hominis* 16S rRNA Probes

| | |
|---|---|
| *Mycoplasma hominis* Probe 2191 (32mer 53% G + C)<br>5'-CGC CGC TAG TTA TTG CTA ACC TCG CTC GAC AT-3' | SEQ ID NO: 14 |
| *Mycoplasma hominis* Probe 2228 (49mer 39% G + C)<br>5'-CCG ACA GTC TGC AAT CAT TTC CTA TTG CAA<br>     ATG TTC TTC CCT TAT AAC T-3' | SEQ ID NO: 15 |
| *Mycoplasma hominis* Probe 2260 (39mer 39% G + C)<br>5'-GGC AGT ATC TCT AGA GTG CTC AAC TTA ATG TTA GTA ACT-3' | SEQ ID NO: 16 |

TABLE 2

*Ureaplasma urealyticum* specific probes Targeting the 16S rRNA

| Strain designation | | Genus/Species | 2262 | 2256 | 2246 | 2218 | 2271 | 2220 | 2259 |
|---|---|---|---|---|---|---|---|---|---|
| serotypes | 1 | *Ureaplasma urealyticum* | + | + | + | + | + | + | + |
| | 2 | *Ureaplasma urealyticum* | + | + | + | + | + | + | + |
| | 3 | *Ureaplasma urealyticum* | + | + | + | + | + | + | + |
| | 4 | *Ureaplasma urealyticum* | + | + | + | + | + | + | + |
| | 5 | *Ureaplasma urealyticum* | + | + | + | + | + | + | + |
| | 6 | *Ureaplasma urealyticum* | + | + | + | + | + | + | + |
| | 7 | *Ureaplasma urealyticum* | + | + | + | + | + | + | + |
| | 8 | *Ureaplasma urealyticum* | + | + | + | + | + | + | + |
| | 9 | *Ureaplasma urealyticum* | + | + | + | + | + | + | + |
| | 10 | *Ureaplasma urealyticum* | + | + | + | + | + | + | + |
| | 11 | *Ureaplasma urealyticum* | + | + | + | + | + | + | + |
| | 12 | *Ureaplasma urealyticum* | + | + | + | + | + | + | + |
| | 13 | *Ureaplasma urealyticum* | + | + | + | + | + | + | + |
| | 14 | *Ureaplasma urealyticum* | + | + | + | + | + | + | + |

TABLE 2-continued

Ureaplasma urealyticum specific probes Targeting the 16S rRNA

| Strain designation | | Genus/Species | 2262 | 2256 | 2246 | 2218 | 2271 | 2220 | 2259 |
|---|---|---|---|---|---|---|---|---|---|
| FH-300 | | Mycoplasma pneumoniae | − | − | − | − | − | − | − |
| PI1428 | | Mycoplasma pneumoniae | − | − | − | − | − | − | − |
| TW10-5P | | Mycoplasma pneumoniae | − | − | − | − | − | − | − |
| TW10-6P | | Mycoplasma pneumoniae | − | − | − | − | − | − | − |
| TW48-5P | | Mycoplasma pneumoniae | − | − | − | − | − | − | − |
| R32-P | | Mycoplasma pneumoniae | − | − | − | − | − | − | − |
| TW8-6P | | Mycoplasma pneumoniae | − | − | − | − | − | − | − |
| TW25-40 | | Mycoplasma pneumoniae | − | − | − | − | − | − | − |
| TW14-4 | | Mycoplasma pneumoniae | − | − | − | − | − | − | − |
| TW11-4 | | Mycoplasma pneumoniae | − | − | − | − | − | − | − |
| 33530 | G-37 | Mycoplasma genitalium | − | − | − | − | − | − | − |
| TW10-5G | | Mycoplasma genitalium | − | − | − | − | − | − | − |
| UTMB-10G | | Mycoplasma genitalium | − | − | − | − | − | − | − |
| 25960 | | Mycoplasma pirum | − | − | − | − | − | − | − |
| 19610 | | Mycoplasma gallisepticum | − | − | − | − | − | − | − |
| 15718 | KS-1 | Mycoplasma putrefaciens | − | − | − | − | − | − | − |
| | PG18 | Mycoplasma fermentans | − | − | − | − | − | − | − |
| | 33552 | Mycoplasma iowae | − | + | − | − | − | − | − |
| | KD735 | Mycoplasma pulmonis | − | − | − | − | − | − | − |
| | | Mycoplasma muris | − | + | − | − | − | − | − |
| | 10 | Mycoplasma hominis | − | − | − | − | − | − | − |
| | 93 | Mycoplasma hominis | − | − | − | − | − | − | − |
| | 132 | Mycoplasma hominis | − | − | − | − | − | − | − |
| | 183 | Mycoplasma hominis | − | − | − | − | − | − | − |
| 23114 | PG21 | Mycoplasma hominis PG21 | − | − | − | − | − | − | − |
| 23206 | PG8 | Acholeplasma laidlawii | − | − | − | − | − | − | − |
| 8090 | | Citrobacter freundii | − | − | − | − | − | − | − |
| 1665 | | Escherichia coli | − | − | − | − | − | − | − |
| 33391 | | Haemophilus influenzae | − | − | − | − | − | − | − |
| 13077 | | Neisseria meningitidis A | − | − | − | − | − | − | − |
| 15955 | | Agrobacterium tumefaciens | − | − | − | − | − | − | − |
| 7757 | | Desulfovibrio desulfuricans | − | − | − | − | − | − | − |
| 33560 | | Camplyobacter jejuni | − | − | − | − | − | − | − |
| 13124 | | Clostridium perfringens | − | − | − | − | − | − | − |
| | | Spirochaeta aurantia | − | − | − | − | − | − | − |
| 25285 | | Bacteroides fragilis | − | − | − | − | − | − | − |
| | | Stool RNA | − | − | − | − | − | − | − |
| | | Wheat Germ | − | − | − | − | − | − | − |
| | | Human CaSKi | − | − | − | − | − | − | − |
| 18804 | | Candida albicans | − | − | − | − | − | − | − |
| 14116 | | Cryptococcus neoformans | − | − | − | − | − | − | − |

TABLE 3

Mycoplasma hominis specific probes Targeting the 16S rRNA

| Strain designation | | Genus/Species | 2191 | 2228 | 2260 |
|---|---|---|---|---|---|
| FH-300 | | Mycoplasma pneumoniae | − | − | − |
| PI1428 | | Mycoplasma pneumoniae | − | − | − |
| TW10-5P | | Mycoplasma pneumoniae | − | − | − |
| TW10-6P | | Mycoplasma pneumoniae | − | − | − |
| TW48-5P | | Mycoplasma pneumoniae | − | − | − |
| R32-P | | Mycoplasma pneumoniae | − | − | − |
| TW8-6P | | Mycoplasma pneumoniae | − | − | − |
| TW25-40 | | Mycoplasma pneumoniae | − | − | − |
| TW14-4 | | Mycoplasma pneumoniae | − | − | + |
| TW11-4 | | Mycoplasma pneumoniae | − | − | + |
| 33530 | G-37 | Mycoplasma genitalium | − | − | − |
| TW10-5G | | Mycoplasma genitalium | − | − | − |
| UTMB-10G | | Mycoplasma genitalium | − | − | − |
| 25960 | | Mycoplasma pirum | − | − | − |
| 19610 | | Mycoplasma gallisepticum | − | − | − |
| 15718 | K1-1 | Mycoplasma putrefaciens | − | − | − |
| | PG18 | Mycoplasma fermentans | +− | +− | +− |
| | 33552 | Mycoplasma iowae | +− | − | − |
| | KD735 | Mycoplasma pulmonis | +− | − | − |
| | | Mycoplasma muris | − | − | − |
| 23114 | PG21 | Mycoplasma hominis PG21 | ++++ | ++++ | ++++ |
| | 10 | Mycoplasma hominis | ++++ | ++++ | ++++ |
| | 93 | Mycoplasma hominis | ++++ | ++++ | ++++ |
| | 132 | Mycoplasma hominis | ++++ | ++++ | ++++ |
| | 183 | Mycoplasma hominis | ++++ | ++++ | ++++ |
| 23206 | PG8 | Acholeplasma laidlawii | − | − | +− |
| | 10 | Ureaplasma urealyticum | − | − | − |
| IG 3224 | | Citrobacter freundii | − | − | − |
| IG 3157 | | Escherichia coli | − | − | − |
| 33391 | | Haemophilus influenzae | − | − | − |
| 13077 | | Neisseria meningitidis A | − | − | − |
| 15955 | | Agrobacterium tumefaciens | − | − | − |
| 7757 | | Deulfovibrio desulfuricans | − | − | − |
| 33560 | | Campylobacter jejuni | − | − | − |
| 13124 | | Clostridium perfringens | − | − | − |
| | | Spirochaeta aurantia | − | − | − |
| 25285 | | Bacterodes fragilis | − | − | − |
| | | Stool RNA | − | − | − |

TABLE 3-continued

Mycoplasma hominis specific probes
Targeting the 16S rRNA

| Strain designation | Genus/Species | 2191 | 2228 | 2260 |
|---|---|---|---|---|
|  | Wheat Germ | – | – | – |
|  | Human CaSKi | – | – | – |
| 18804 | Candida albicans | – | – | – |
| 14116 | Cryptococcus neoformans | – | – | – |

TABLE 4

Mycoplasma genitalium specific probes
Targeting the 16S rRNA

| Strain designation | | Genus/Species | 2227 | 2219 |
|---|---|---|---|---|
| PH-300 | | Mycoplasma pneumoniae | +– | ++++ |
| PI1428 | | Mycoplasma pneumoniae | +– | ++++ |
| TW10-5P | | Mycoplasma pneumoniae | +– | ++++ |
| TW10-6P | | Mycoplasma pneumoniae | +– | ++++ |
| Tw48-5P | | Mycoplasma pneumoniae | +– | ++++ |
| R32-P | | Mycoplasma pneumoniae | +– | ++++ |
| TW8-6P | | Mycoplasma pneumoniae | +– | ++++ |
| TW25-40 | | Mycoplasma pneumoniae | +– | ++++ |
| TW14-4 | | Mycoplasma pneumoniae | +– | ++++ |
| TW11-4 | | Mycoplasma pneumoniae | +– | ++++ |
| 33530 | G-37 | Mycoplasma genitalium | ++++ | ++++ |
| TW10-5G | | Mycoplasma genitalium | ++++ | ++++ |
| UTMB-10G | | Mycoplasma genitalium | ++++ | ++++ |
| PG18 | | Mycoplasma fermentans | – | – |
| 33552 | | Mycoplasma iowae | – | – |
| KD735 | | Mycoplasma pulmonis | – | – |
| 25960 | | Mycoplasma pirum | +– | – |
| 19610 | | Mycoplasma gallisepticum | +– | – |
| 23114 | PG21 | Mycoplasma hominis PG21 | – | – |
| 15718 | KS-1 | Mycoplasma putrefaciens | – | – |
| serotype 8 | | Ureaplasma urealyticum | – | – |
| 23206 | PG8 | Acholeplasma laidlawii | – | – |
| IG 3224 | | Citrobacter freundii | – | – |
| IG 3157 | | Escherichia coli | – | – |
| 33391 | | Haemophilus influenzae | – | – |
| 13077 | | Neisseria meningitidis A | – | – |
| 15955 | | Agrobacterium tumefaciens | – | – |
| 7757 | | Desulfovibrio desulfuricans | – | – |
| 33560 | | Campylobacter jejuni | – | – |
| 13124 | | Clostridium perfringens | – | – |
|  | | Spirochaeta aurantia | – | – |
| 25285 | | Bacteroides fragilis | – | – |
|  | | Stool RNA | – | – |
|  | | Wheat Germ | – | – |
|  | | Human CaSKi | – | – |
| 18804 | | Candida albicans | – | – |
| 32045 | | Cryptococcus neoformans | – | – |

TABLE 5

Mycoplasma genitalium specific probes
Targeting the 23S rRNA

| Strain designaton | | Genus/Species | 2335 | 2337 | 2334 | 2336 |
|---|---|---|---|---|---|---|
| FH-300 | | Mycoplasma pneumoniae | – | – | – | – |
| PI1428 | | Mycoplasma pneumoniae | – | – | – | – |
| TW10-5P | | Mycoplasma pneumoniae | – | – | – | – |
| TW10-6P | | Mycoplasma pneumoniae | – | – | – | – |
| TW48-5P | | Mycoplasma pneumoniae | – | – | – | – |
| R32-P | | Mycoplasma pneumoniae | – | – | – | – |
| TW8-6P | | Mycoplasma pneumoniae | – | – | – | – |
| TW25-40 | | Mycoplasma pneumoniae | – | – | – | – |
| TW14-4 | | Mycoplasma pneumoniae | – | – | – | – |
| TW11-4 | | Mycoplasma pneumoniae | – | – | – | – |
| 33530 | G-37 | Mycoplasma genitalium | ++++ | ++++ | ++++ | ++ |
| TW10-5G | | Mycoplasma genitalium | ++++ | ++++ | ++++ | +++ |
| UTMB-10G | | Mycoplasma genitalium | ++++ | ++++ | ++++ | +++ |
| 25960 | | Mycoplasma pirum | – | – | – | – |
| 19610 | | Mycoplasma gallisepticum | – | – | – | – |
| 23114 | PG21 | Mycoplasma hominis PG21 | – | – | – | – |
| 15718 | KS-1 | Mycoplasma putrefaciens | – | – | – | – |
|  | PG18 | Mycoplasma fermentans | – | – | – | – |
| 33552 | | Mycoplasma iowae | – | – | – | – |
| KD735 | | Mycoplasma pulmonis | – | – | – | – |
| 23206 | PG8 | Acholeplasma laidlawii | – | – | – | – |
| IG 3224 | | Citrobacter freundii | – | – | – | – |
| IG 3157 | | Escherichia coli | – | – | – | – |
| 33391 | | Haemophilus influenzae | – | – | – | – |
| 13077 | | Neisseria meningitidis A | – | – | – | – |
| 15955 | | Agrobacterium tumefaciens | – | – | – | – |
| 7757 | | Desulfovibrio desulfuricans | – | – | – | – |
| 33560 | | Campylobacter jejuni | – | – | – | – |
| 13124 | | Clostridium pefringens | – | – | – | – |
|  | | Spirochaeta aurantia | – | – | – | – |
| 25285 | | Bacteroides fragilis | – | – | – | – |
|  | | Stool RNA | – | – | – | – |
|  | | Wheat Germ | – | – | – | – |
|  | | Human CaSKi | – | – | – | – |
| 18804 | | Candida albicans | – | – | – | – |
| 14116 | | Cryptococcus neoformans | – | – | – | – |

What is claimed is:

1. A composition consisting of nucleic acids containing 10 to 250 nucleotides which hybridize under identical conditions to rRNA or rDNA of pathogenic *Mycoplasma genitalium* bacteria and not to rRNA or rDNA of nonmycoplasma bacteria in humans wherein the nucleic acids are complementary or homologous to a sequence comprising any ten consecutive nucleotides with a nucleic acid sequence selected from the group consisting of sequences 2262 (SEQ ID NO: 1), 2256 (SEQ ID NO: 2), 2246 (SEQ ID NO: 3), 2218 (SEQ ID NO: 4), 2271 (SEQ ID NO: 5), 2220 (SEQ ID NO: 6), 2259 (SEQ ID NO: 7), 2227 (SEQ ID NO: 8), 2335 (SEQ ID NO: 10), 2337 (SEQ ID NO: 11), 2334 (SEQ ID NO: 12), 2336 (SEQ ID NO: 13), 2191 (SEQ ID NO: 14), 2228 (SEQ ID NO: 15), and 2260 (SEQ ID NO: 16) and (2) complementary or homologous with at least one region of rRNA or rDNA selected from the group of regions consisting of positions 1110 to 1160 of the *Mycoplasma genitalium* 16S rRNA, and positions 260 to 330, 1590 to 1630, and 1850 to 1900 of *Mycoplasma genitalium* 23S rRNA, and such numerical designations are nucleotide positions counted from the 5' end of the RNA molecule.

2. As an article of manufacture, a set of at least two nucleic acid compositions, each nucleic acid composition having approximately 10 to approximately 250 nucleotides of different sequence compositions, which hybridize under identical conditions to rRNA or rDNA of pathogenic *mycoplasma genitalium* bacteria associated with the human urinary tract and genital areas and not to rRNA or rDNA of nonmycoplasma bacteria of humans, wherein (1) each nucleic acid composition set is selected from the group consisting of probe 2335 (SEQ ID NO: 10) and probe 2337 (SEQ ID NO: 11); probe 2335 (SEQ ID NO: 10) and probe 2334 (SEQ ID NO: 12); probe 2334 (SEQ ID NO: 12) and probe 2336 (SEQ ID NO: 13); and probe 2227 (SEQ ID NO: 8) and probe 2219 (SEQ ID NO: 9) an their complements and (2) complementary to or homogous with at least one region of rRNA and rDNA selected from the group of regions consisting of positions 1110 to 1160 of *Mycoplasma genitalium* 16S rRNA, and positions 260 to 330, 1590 to 1630, and 1850 to 1900 of *Mycoplasma genitalium* 23S rRNA and such numerical designations are nucleotide positions counted from the 5' end of the RNA molecule.

3. The composition of claim 1 wherein the nucleic acids hybridize to a region of 16S rRNA or 16S rDNA of *Mycoplasma genitalium* selected from the group of positions consisting of 1100 to 1160.

4. The composition of claim 1 wherein the nucleic acids hybridize to a region of 16S rRNA or 23S rDNA of *Mycoplasma genitalium* selected from the group of positions consisting of 260 to 330, 1590 to 1630 and 1850 to 1900.

5. The article of manufacture of claim 2 wherein said set is selected from the group of nucleic acid composition sets, defined by probes, probe 2227 and probe 2219, and their complements, said set for detecting *Mycoplasma genitalium*.

6. The article of manufacture of claim 2 wherein said set is selected from the group of nucleic acid composition sets, defined by probes, probe 2335 and probe 2337;

probe 2335 and probe 2334;

probe 2334 and probe 2336 and their complements, said set for detecting *Mycoplasma genitalium*.

7. A kit for detecting the presence of *Mycoplasma genitalium*, comprising nucleic acids having 10 to 250 nucleotides capable of hybridizing to rRNA or rDNA of *Mycoplasma genitalium* in preference to rRNA or rDNA of humans, fungi and other Mycoplasma wherein said nucleic acids are complementary or homologous to at least one region of rRNA or rDNA selected from the group of regions consisting of positions 1110 to 1160 of *Mycoplasma genitalium* 16S rRNA and positions 260 to 330, 1590 to 1630, and 1850 to 1900 of *Mycoplasma genitalium* 23S rRNA and such numerical designations are nucleotide positions counted from the 5' end of the RNA molecule.

8. The article of manufacture of claim 2, wherein said set is selected from the group of nucleic acid composition sets, defined by probes, probe 2335 (Sequence No. 10) and probe 2337 (Sequence No. 11);

probe 2335 (Sequence No. 10) and probe 2334 (Sequence No. 12);

probe 2334 (Sequence No. 12) and probe 2336 (Sequence No. 13); and their complements, said set for detecting *Mycoplasma genitalium*.

9. The article of manufacture of claim 2, wherein said set is selected from the group of nucleic acid composition sets, defined by probes, probe 2227 (Sequence No. 8) and probe 2219 (Sequence No. 9), and their complements, said set for detecting *Mycoplasma genitalium*.

10. A method of detecting *Mycoplasma genitalium* in a sample comprising:

a) contacting said sample with at least one nucleic acid composition having 10 to 250 nucleotides which, under conditions that allow said nucleic acid compositions to hybridize, hybridize under identical conditions, to rRNA or rDNA of said mycoplasma organism and not to rRNA or rDNA of nonmycoplasma bacteria, b) imposing hybridization conditions on said sample to form a hybridization product in the presence of target; and c) detecting said hybridization product as an indication of the presence of said mycoplasma, wherein the nucleic acid composition of said contacting step is complementary to or homologous with any 10 consecutive nucleotides selected from the group consisting of sequences defined by probes consisting of 2219 (Sequence No. 9), 2227 (Sequence No. 8), 2335 (Sequence No. 10), 2337 (Sequence No. 11), 2334 (Sequence No. 12), and 2336 (Sequence No. 13), wherein the nucleic acids of said nucleic acid composition are complementary to or homologous with at least one region of rRNA or rDNA selected from the group of regions consisting of positions 1110 to 1160 of *Mycoplasma genitalium* 16S rRNA and positions 260 to 330, 1590 to 1630, and 1850 to 1900 of the *Mycoplasma genitalium* 23S rRNA and such numerical designations are nucleotide positions counted from the 5' end of the RNA molecule.

11. A method for detecting *Mycoplasma genitalium* in a sample comprising:

a) contacting said sample with at least one nucleic acid composition having 10 to 250 nucleotides which, under conditions that allow said nucleic acid composition to hybridize, hybridize preferentially, to rRNA or rDNA of said mycoplasma organism, b) imposing hybridization conditions on said sample to form a hybridization product in the presence of target; and, c) detecting said hybridization product as an indication of the presence of said mycoplasma.

* * * * *